(12) United States Patent
Riess et al.

(10) Patent No.: US 8,750,956 B2
(45) Date of Patent: Jun. 10, 2014

(54) METHOD AND DEVICES FOR ITS EMPLOY FOR REDUCING DISEASE-TRANSFER RISKS

(75) Inventors: Edward Allen Riess, Cincinnati, OH (US); Carroll E. Weller, Mason, OH (US)

(73) Assignee: Edward Allen Riess, Cincinnati, OH (US)

( * ) Notice: Subject to any disclaimer, the term of this patent is extended or adjusted under 35 U.S.C. 154(b) by 0 days.

(21) Appl. No.: 13/602,072

(22) Filed: Aug. 31, 2012

(65) Prior Publication Data

US 2013/0237790 A1    Sep. 12, 2013

Related U.S. Application Data

(60) Provisional application No. 61/537,417, filed on Sep. 21, 2011.

(51) Int. Cl.
*A61B 5/0492*   (2006.01)
(52) U.S. Cl.
USPC ........... 600/373; 600/392; 600/546; 600/548; 206/365; 206/813
(58) Field of Classification Search
USPC ......... 206/365, 366, 380, 813, 820, 824, 828; 600/372, 373, 546, 547, 548, 391, 392; 607/116, 117; 428/911
See application file for complete search history.

(56) References Cited

U.S. PATENT DOCUMENTS

| | | | | |
|---|---|---|---|---|
| 3,944,069 A * | 3/1976 | Eldridge, Jr. | ............. | 206/350 |
| 4,543,958 A * | 10/1985 | Cartmell | ............. | 600/391 |
| 4,758,229 A * | 7/1988 | Doerschner | ............. | 604/187 |
| 4,838,273 A * | 6/1989 | Cartmell | ............. | 600/385 |
| 4,859,515 A * | 8/1989 | Pothetes | ............. | 428/41.7 |
| 5,181,609 A * | 1/1993 | Spielmann et al. | ............. | 206/370 |
| 5,390,671 A * | 2/1995 | Lord et al. | ............. | 600/347 |
| 6,076,002 A * | 6/2000 | Cartmell et al. | ............. | 600/372 |
| 8,172,104 B2 * | 5/2012 | Weber | ............. | 220/62 |
| 2001/0021869 A1 * | 9/2001 | Bishay et al. | ............. | 607/116 |
| 2003/0195599 A1 * | 10/2003 | Bishay | ............. | 607/116 |
| 2008/0064944 A1 * | 3/2008 | VanAntwerp et al. | ............. | 600/373 |
| 2011/0168592 A1 * | 7/2011 | Sakuragi | ............. | 206/366 |

OTHER PUBLICATIONS

Marea Enterprises, Inc "A recommended universal protocol for preventing needlesticks to all allied healthcare workers in perioperative settings where intraoperative neurophysiological monitoring with subdermal needle electrodes is performed" (2012).*
Marea Enterprises, Inc. "NeedleTape" product guide (2012).*

* cited by examiner

*Primary Examiner* — Linda Dvorak
*Assistant Examiner* — Erin M Cardinal

(57) ABSTRACT

The present invention is a method and apparatus, in several embodiments, for providing protection in workplaces in which workers can be exposed to diseases and other contaminations from skin abrasions or punctures by contaminated objects. In its primary application it provides such protection at skin surfaces of healthcare patients into which needle electrodes have been inserted and, under certain conditions, can emerge. This bio-hazard occurs most often during patient-positioning when patients are unconscious due to anesthesia or other reasons. Protection is supplied in the first embodiment by a puncture-resistant head-covering; in the second by a pad that covers and secures needle electrodes, and; in a third as a tissue-penetrating, less hazardous stick-on electrode. The latter two embodiments have pressure-sensitive-adhesive coatings for adhesion to a patient's skin.

7 Claims, 6 Drawing Sheets

120

121  122

METHOD AND DEVICES FOR ITS EMPLOY FOR REDUCING DISEASE-TRANSFER RISKS

TECHNICAL FIELD

This invention relates to the field of medical patient monitoring, and most specifically to the field of Neurodiagnostic Intraoperative Monitoring. It also relates to protective coverings, printed guides, instructions, warnings, and safety devices. Possible classes within which this invention is thought to have relevance are the following:
2 APPAREL, SUBCLASS 455 GUARD OR PROTECTOR, SUBCLASS 2.5 PENETRATION RESISTANT
428 STOCK MATERIAL OR MISCELLANEOUS ARTICLES
442 FABRIC (WOVEN, KNITTED, OR NONWOVEN TEXTILE OR CLOTH, ETC.)
160 FLEXIBLE OR PORTABLE CLOSURE, PARTITION, OR PANEL D24 MEDICAL AND LABORATORY EQUIPMENT
270 SHEET-MATERIAL ASSOCIATING 128 SURGERY
600 SURGERY
604 SURGERY
606 SURGERY
D99 MISCELLANEOUS
Referenced patents: None

BACKGROUND

A needlestick injury can be a scraping or piercing wound typically caused by an accidental encounter with the sharp point of a needle. Needlestick injuries are an occupational hazard in the medical community because they can cause transmission of blood-borne diseases. Some of the more threatening of these diseases are the hepatitis B virus (HBV), the hepatitis C virus (HCV), and the Human Immunodeficiency Virus (HIV), the virus which causes AIDS.

Protocols exist for reporting needlestick injuries in medical environments but for a variety of reasons they are frequently ignored. As a result, a true accounting of these injuries is not available. Rather than delay ongoing medical procedures when experiencing a needlestick, healthcare workers often gamble with the odds of contracting a blood-borne disease and take no action. At least half of such events go unreported because injured healthcare workers downplay the risks, or fear stigmatization and professional consequences[1]. Indeed, in a survey of 255 responders to a questionnaire submitted via e-mail to all staff in a National Health Service trust, where results were compared to occupational health department (OHD) records, 135 (53%) completed the questionnaire and the results revealed that fifteen of 31 consultants (48%), 12/36 junior doctors (33%), 0/39 midwives (0%), and 8/30 theatre staff (27%) reported having had at least one intraoperative needlestick injury during the previous year. Ninety-three percent of consultants, 67% of junior doctors, and 13% of theatre staff had not complied with local protocols. The reasons given were stated to be the length of time it takes to do so (48%) and a perceived low infection risk of the patient (78%) suggesting that a maximum of 16% of intraoperative needlestick injuries were dealt with in accordance to local policy[7].

Years ago, as authorities became aware of this tendency, new rules and guidelines were issued to reduce the incidence of such injuries, the majority of which were considered preventable. Still, worldwide needlestick injuries were estimated to have transmitted 16,000 HCV, 66,000 HBV, and 1,000 HIV infections in the year 2000 among healthcare workers, with attributions due to these injuries constituting approximately 39%, 37%, and 4.4% respectively[2].

Many needlestick injuries are caused by accidental encounters with solid needle electrodes that are placed in patients' bodies for intraoperative monitoring purposes. These incidents generally occur in the operating room where the OR staff is at risk of such injuries when moving and positioning anesthetized patients before, after, and during their surgeries. Skin punctures from these solid needle electrodes are thought to account for less than half of these incidents, but that may be a gross underestimation because needlesticks from needle electrodes are known to be less effective in transferring disease than needles that are hollow—such as hypodermic needles and sharp percutaneous instruments—so brushing-off these injuries is far more common.

Anesthesia personnel are especially vulnerable since they often work on or around the head of a patient to do things such as adjust the airway, relocate a temperature sensor, or assist the surgeon by pulling on the patient's head to open the spaces between the vertebrae, all while the patient's head may be harboring more than a half-dozen subdermal needle electrodes placed at widely separated locations. Needle electrodes in patients' heads are often not visible due to their being covered by hair, making them 'easy to miss'.

The accidental encounter generally occurs when an unsuspecting surgeon, anesthesiologist, surgeon's assistant (SA), nurse anesthetist (CRNA or RNSA), nurse (RN), or other staff member either brushes-against or applies force to reposition a patient and receives a skin-puncture from a subdermal needle electrode in the process. This kind of needlestick injury usually occurs when the electrode, due to this applied pressure, has its sharp end forced outward through the patient's skin and through the medical-grade adhesive tape that is normally used to cover the electrode and hold it in place. Naturally, all of the variety of adhesive tapes used in the OR are easily punctured and offer no protection in these circumstances.

Although needlestick injuries typically cause only minor bleeding and visible trauma, the risk of viral infection obviously exists. Not so obviously, a needlestick injury can put a patient at risk if the injured health professional carries a disease since the needle's tip reenters the patient's subdermal tissue, once the applied pressure is removed, and is dragged through more of the patient's tissue when it is withdrawn. In addition, when needle electrodes are removed from patients, they are sometimes mishandled and left on tables or the floor due to haste or forgetfulness and, instead of being put into sharps containers, nurses and rushed cleanup crews fail to recognize the discarded wires as having needles on their ends and they sometimes become stuck. When they are not recognized as needle electrodes and are thought to simply be wires that are to be discarded, the needle electrodes are sometimes placed in normal refuse containers where they pose a risk to unsuspecting garbage handlers. It should be understood that these needles remain hazardous well after their liquid contamination has dried. Although the infectiousness of both HIV and HCV decreases within a couple of hours, the infectiousness of HBV remains stable during desiccation and remains infectious for more than a week[3].

After a needlestick injury, a protocol, with its specified procedures, should be followed to minimize the risk of infection. When the affected person follows protocol and reports the injury, it results in a loss of time for both the affected person and the facility in which the injury occurred. Taking care of each reported needlestick injury is estimated to cost institutions about $2,500 in the short term in the US[4]. Immediately following the injury, the affected area is supposed to be rinsed and washed thoroughly with soap and water without "milking-out" blood from the wound (per a recommendation of the CDC). Unless the potential source is known to be negative for HBV, HCV, and HIV, post-exposure prophylaxis (PEP) is supposed to be initiated, ideally within one hour of the injury[6]. Typically this is done in the emergency department or the occupational health office. Soon afterward, lab tests of the injured party are obtained for baseline studies for HIV and an acute hepatitis panel and, for immunized individuals, also for HB surface antibody; further, the status of the potential source of pathogens, unless already known, is similarly tested[5]. Follow-up of exposed individuals includes HIV testing by enzyme immunoassay to monitor for possible seroconversion for at least 6 months after exposure, and counseling[1].

Despite these dangers, there is currently no readily available product that can significantly reduce or eliminate the risk of needlestick injury from needle electrodes. Securing needle electrodes to patients' bodies with a thick, foam tape is a procedure that is occasionally used to provide a small amount of protection since it increases the distance between the needle tip and the OR staff, presents a squeegee action to the needle as it passes through the tape, and, to some degree, distributes contact forces over a larger area. The lack of a truly effective product, however, is certainly the main reason that punctures from electrode needles are as common as they are in cases where intraoperative monitoring is employed. Indeed, three needlestick events occurred from inserted subdermal needle electrodes that were used during one intraoperatively monitored surgical procedure at one hospital in Cincinnati in early 2011, and the news of that situation spread rapidly throughout the Perioperative Surgery department.

To address the need for, and to provide the benefits of a system that could greatly reduce or even eliminate the risk of needle-electrode needlesticks among OR and other hospital staff, the present product was invented to provide puncture-resistant barriers wherever needlestick-susceptibility exists. The use of this product would greatly reduce the chances that the highly sharpened ends of needle electrodes would be able to threaten healthcare workers.

For protection from needle electrodes that are inserted into patients' heads and often not secured by lengths of tape, a first embodiment of the present invention was devised as an appliance in the form of a substantially thin and generally flexible puncture-resistant "hat" that can cover all regions of the head into which needle electrodes are typically inserted. This hat is lightly kept in-place preferably with embedded or attached elastic material.

For protection from needle electrodes that are inserted into generally hairless regions of patients' bodies, the present invention is a device which incorporates a puncture-resistant barrier, and a self-adhesive-material coating on at least a portion of its underside region for easy attachment to the patient and for securing the electrode lead(s). The self-adhesive material will generally be a medical-grade pressure-sensitive-adhesive which adheres with the application of light pressure. The device can be packaged the way EKG stick-on electrodes are supplied in quantities, nested together on a larger release-material-covered flexible sheet for easy peel-off at the time of use. In a similar fashion, it can be packaged in quantities, nested together in a linear array on a similar type of substrate (of width sufficient to cover, for example, the narrower dimension of the device, and of length sufficient to support any number of the devices) which can be rolled into a roll resembling a roll of tape, enabling the product to be sold in the form of a roll of multiple devices from which individual devices may be conveniently peeled, manually or automatically from a dispenser. In addition, intervening sections of both the flat-sheet and rolled substrates can be perforated so that individual devices may be easily separated from others on their common substrates by tearing the substrates at the perforations.

A third embodiment of the present invention reduces the danger of needlesticks by replacing the needle electrodes with an entirely new type of monitoring electrode that can be made with a hard-wired lead, similar to the hard-wired lead of a needle electrode, or it can be made with a connector "button" to which a snap-on electrode lead can be attached in much the same way that a snap-on electrode lead connects to a stick-on EEG electrode. Each configuration of this third embodiment requires sterilization and sterile packaging since they incorporate several relatively short, skin-piercing needles (resembling the group of needles on the insulation-piercing component in alligator clips of telephone-repairperson's handsets), or other skin-puncturing implements, that are part of a component that is attached to its adhesive-bearing underside surface. This component is either mounted flat against the undersurface or it is supported by a flexible conductive strap that can preferably be corrugated or folded-back-onto itself and implemented to prevent subtle movements of the pad from affecting the penetration-depth of the needles. (Skin-penetration makes the low-impedance body-contact that is so important in achieving the high degree of common-mode-signal-rejection that enables acquisition of microvolt-level biological signals in the presence of electrical interference.) Advantages of this third embodiment include (1) easier attachment to the patient, (2) a substantial reduction or elimination of needlestick-injury-risk associated with needle electrodes since detaching and discarding these models could be safely accomplished by attaching them to each other or attaching them to a discardable penetration-resistant film or sheet, supplied and packaged with them as safe disposal aids, and (3) for the snap-connected models, reduced cost of electrodes due to the reusability of the snap-on leads. This second advantage can be contrasted with the task of removing needle electrodes where their thin, sharp needles are held by their leads during removal after which they can (and too-frequently do) "fly-around" and puncture the skin of anyone nearby.

A fourth embodiment of the present invention is envisioned and would be like the third except that in place of physical skin-penetrating components it would use an electrically conductive chemical or chemical compound that penetrates the skin's dermal layer to achieve a higher degree of electrical conductivity than is possible with conventional stick-on EEG electrodes. Similarly, advantages of this embodiment would include (1) reduced cost of electrodes due to the reusability of the snap-on leads, (2) easier patient attachment, and (3) complete elimination of needlestick-injury-risk since no mechanical penetration of the patient's skin occurs with its use. This embodiment would require sterilization and sterile packaging.

Disclosure

Every day, in hospitals and clinics around the world, needle-electrodes are inserted into patients for electrical stimulation and/or recording of bioelectric potentials. In the operating room (OR), the standard of care for a variety of surgeries involves electrophysiological monitoring for which needle-electrodes are often required to obtain good-connection and near-contact-impedance uniformity. These needle-electrodes are most commonly inserted in such a way that their shanks occupy spaces just beneath and nearly parallel to the patient's dermal skin-tissue. These electrodes have typical diameters in the neighborhood of 0.013 inches and their pointed tips are extremely sharp.

As mentioned in the previous section, medical personnel frequently need to hold, position, and move the bodies of their patients. When they are in the OR, patients are often moved when their bodies are limp from the effects of general anesthesia and in these situations, considerable pressures are applied to areas of patients' skin tissues. These forces can act on the needle-electrodes in such a way that their sharp ends are forced through and out of the patient's skin and into the bodies of medical personnel who consequently can become exposed to foreign organisms and diseases from the patient's biological tissues and fluids.

To improve this situation, the current invention was developed to enhance environmental safety for medical personnel and to greatly reduce the financial losses associated with both the needlestick-injury protocols and the medical problems that result from exposures to fluid- and tissue-born organisms and diseases. The protection would be provided by a puncture-resistant material that could resist penetration by needle electrodes. A search for such materials produced a long list that first looked promising: BioSteel®; single or multiple layers of DuPont™ Kevlar® aromatic polyamide organic fibers (especially Correctional™ fiber style 779, a high-strength, high-modulus, thermally stable material which resists forces that push fibers apart); CoreTek® fiber; multiple layers of a "SuperFabric" such as that used in HexArmour Gloves; a Kevlar®-based fabric known as "TurtleSkin"; the textile composite Rhinoguard™ [having EN388 level 4 Puncture Resistance and ASTM F1342-05 (modified) medical (pointed)-needle-test rating of 4.1 Newtons (0.92 lbs)]; and even genetically altered silkworm fibers. To meet the need of resisting needles that could experience much more than one pound of driving force, however, and to achieve reduced thickness and numbers of layers, better materials have been evaluated and these have included wire mesh, composite materials, solid metal particles, ceramic-bearing materials, silica nano-sized plates, rods, and functionalized nanoparticles, permeable nano-sized mica plates, and blended, compacted, and sintered metal powders mixed with alloys to produce homogeneous blends of ingredients[8]. Some of these and others remain proprietary so cannot be listed in this discussion.

As a protection device for needle electrodes that are inserted into patients' heads, a first embodiment of the present invention was created as an appliance in the form of a thin and generally flexible puncture-resistant head-covering, or hat, that can cover the majority of a patient's head. Recommended for this model is the addition of appropriate words in suitable languages in multiple areas of the hat, in large red letters against a white or other light-colored background, such as "SHARPS UNDERNEATH". When in use, the hat is preferably kept in-place with embedded or attached elastic material.

As a protection device for needle electrodes that are inserted into patients' bodies, the present invention was created as a thin, flexible pad substantially made from, or incorporating, a puncture-resistant barrier that has a self-adhesive-material coating on at least a portion of one side. The puncture-resistant barrier can be composed of numerous types of materials and for some, a supporting layer of flexible material is required for its support. This supporting layer is preferably made from latex-free and hypoallergenic paper, plastic film, cloth, metal foil, or other suitable material (such as fiberglass) that can support one or more single- or multiple-layer puncture-resistant components. Additionally, when electrode leads are secured to the patient with staples, these devices would still be useful to prevent needlesticks making their employment in these situations no less valuable in reducing the associated risk of injury. For both of these models appropriate warnings, such as "SHARPS UNDERNEATH" in red letters against a white background, are expected to be useful markings in their employment.

A third embodiment of the present invention achieves low-impedance subdermal electrical contact with patients through skin-puncturing components that pose a lower risk for needlestick than do needle electrodes. This embodiment preferably has approximately the form and shape of a stick-on EEG electrode, using a hard-wired lead or a roughly ball-shaped contact on its top-side surface for accepting the snap-on connector of a reusable snap-on electrode lead. It also has a pressure-sensitive-adhesive region, generally in the peripheral regions of its bottom-side surface. Instead of making a low-grade electrical contact with the patient's skin through a conductive gel in the center region of its bottom surface (as is the case for typical stick-on EEG electrodes) it makes subdermal electrical contact with the patient through one or more very short needles (resembling the group of needles on the insulation-piercing component in alligator clips of telephone-repairperson's handsets) or other skin-piercing components that protrude preferably from the region that would be otherwise be occupied by the conductive gel. These skin-piercing components are supported preferably via a flexible conductive strap that is preferably corrugated, folded-back on itself, and implemented in such a way that it prevents the pad's subtle movements or partial disengagement from affecting the penetration-depth of the skin-piercing components. Advantages of this third embodiment include (1) a reduced cost of electrodes due to the reusability of the snap-on leads, (2) easier attachment to the patient, and (3) a substantial reduction of needlestick-injury-risk associated with subdermal patient-connection since detachment of the appliance of this embodiment can be more easily controlled (for example, by "sticking" the adhesive-coated surfaces to each other as they are removed, or sticking them to a discardable penetration-resistant film or sheet supplied and packaged with the appliances as a safe disposal aid). This third embodiment does not require a puncture-resistant material but since it is physically invasive, it does require sterilization and sterile packaging. Since it contains sharp objects, or "sharps", it's advisable that the in-use visible surface carry an appropriate warning, such as "SHARPS UNDERNEATH" in red letters against a white background, with the words occupying each of two semicircular regions near the edge for round-shaped models, or otherwise attention-getting formats for otherwise-shaped models.

A fourth embodiment of the present invention, envisioned for further study, would achieve low-impedance subdermal electrical contact with patients through a chemical skin-penetration means. This embodiment also preferably would have approximately the form and shape of a stick-on EEG electrode, using a hard-wired lead or a roughly ball-shaped contact on its top-side surface for accepting the snap-on connector of a reusable snap-on electrode lead. Similarly, it also would have a pressure-sensitive-adhesive region, generally in the peripheral regions of its bottom-side surface. It would make subdermal electrical contact with the patient through a chemical or chemicals that enable an exchange of electrons or ions with, for example, an interstitial pad wetted with DMSO HP—[Dimethylsulfoxide High Purity, CH3SOCH3, Electrical conductivity (20° C.) 10-8 W-1 cm-1] or DMSO solution with dissolved chemicals. Advantages of this fourth embodiment similarly would include (1) a reduced cost of electrodes due to the reusability of the snap-on leads, (2) easier attachment to the patient, and (3) a complete elimination of needlestick-injury-risk associated with this form of subdermal patient-connection since no physical penetration of the patient's skin occurs with its use. This embodiment would likely not require sterilization or sterile packaging.

The components of all embodiments would ideally be, or be fashioned from, materials that are currently FDA-approved or easily FDA-approvable and suitable for use in the OR and other medical settings. In addition, all embodiments could be designed and constructed in any way desired provided that their characteristics generally facilitate ease of use, performance efficacy, cost-effective design-for-manufacturability, and packaging suitable to a medical device. For example, the flexible pad is preferably designed with one or more non-stick tabs for ease of handling and removal, and the pad can be supplied on a reel to facilitate rapid peel-off. Alternatively, the pad can be designed to be deliverable by a belt-worn dispenser to eliminate the frequently cumbersome and time-consuming task of tearing-off lengths of adhesive tape (that often requires locating a difficult-to-find end, starting its separation with a fingernail, and extracting and separating a suitable length by cutting, tearing, or drawing it against a serrated edge).

Other means for achieving low-impedance contact with a patient in the apparatus of the third-embodiment, such as using lengths of shallowly penetrating blade-elements, singly or in conjunction with the mentioned ion-exchanging chemicals, are considered obvious extensions of the art and therefore within the scope of this invention.

As new products that have not previously existed, all of these embodiments and models, which serve the single purpose of preventing needlesticks, primarily from needle electrodes, would provide a worthwhile profit stream for a manufacturer from their sales as consumables. Compared to the products they would obviate, their usages would (1) reduce disease-transfer due to needlestick injuries, and (2) lower the incidence and costs (in both time and money) associated with needlesticks (which include at a minimum, the time and monetary costs of blood tests, acquiring permissions for testing the patient, overtime costs of staff needed to cover down-time of the injured, prophylactic immunizations, and vaccination regimens).

A primary design-focus of the present invention has been continuous recognition that all models must meet requirements of the United States Food and Drug Administration and perhaps also the Joint Committee on Accreditation of Healthcare Organizations (JHACO), and specific hospital Internal Review Boards that exist to approve devices that are to be used in the operating room. In view of such requirements along with the desire to achieve near-optimal puncture-resistance, it should be expected that first models would be constructed with currently available products and that improvements would be made for future models. Acquiring or ensuring FDA approval in advance for candidate materials such as functionalized silica, mica plates, highly flexible TPU or TPE thermoplastics, thermoset elastomers, and appropriate adhesives will accelerate product development under this plan.

The following is a general list of specifications that apply to one or more of the embodiments and models described above.
Product Stock/Purchase Category—consumable
Product Deployment—adjunctive, hand-applied

Figure 2:
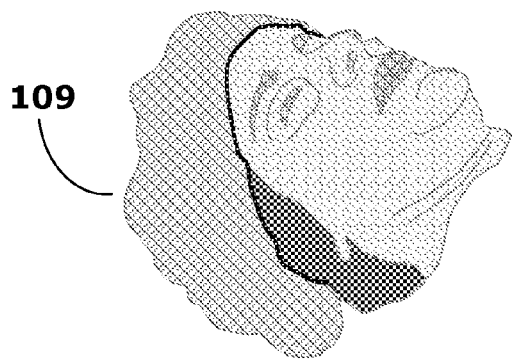

The first embodiment of the present invention is illustrated in FIG. 2. It is an appliance in the form of a substantially thin and generally flexible puncture-resistant hat 109 that can be kept in-place with embedded or attached elastic material that spans the periphery of its opening. The hat can be fabricated from puncture-resistant material such as those mentioned earlier, or even from a tightly woven wire-mesh screen. If the material is sufficiently electrically conductive an advantage would be realized in the acquisition of bioelectric signals derived from head electrodes since the hat would act as a shield over regions where the electrode leads travel through different regions of physical space where common-mode interference cannot be canceled in the way it is automatically canceled when the recording leads occupy approximately the same physical space. The maximum advantage would occur if the metal mesh were grounded but this would likely not be an allowable practice in the operating room unless the entirety of the contactable surface of the hat were insulated from its conductive part.

Figure 1:
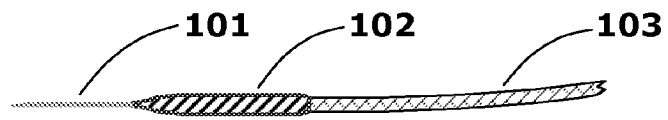
FIG. 1 is an illustration of a conventional subdermal needle electrode having components of a sharp-tipped needle 101 (typically 0.013 inches in diameter), a flexible insulated wire 103, a robust bonding of these two components ensuring a stable low-resistance electrical connection (not visible), and an insulated covering for this bonding region 102. This type of electrode is typically inserted just under the surface of, and nearly parallel to the skin.
Figure 3:
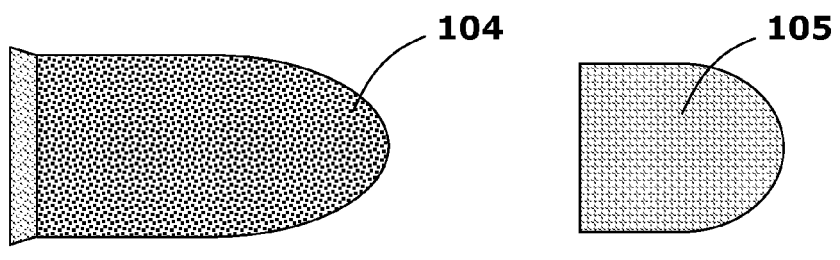
Figure 3:
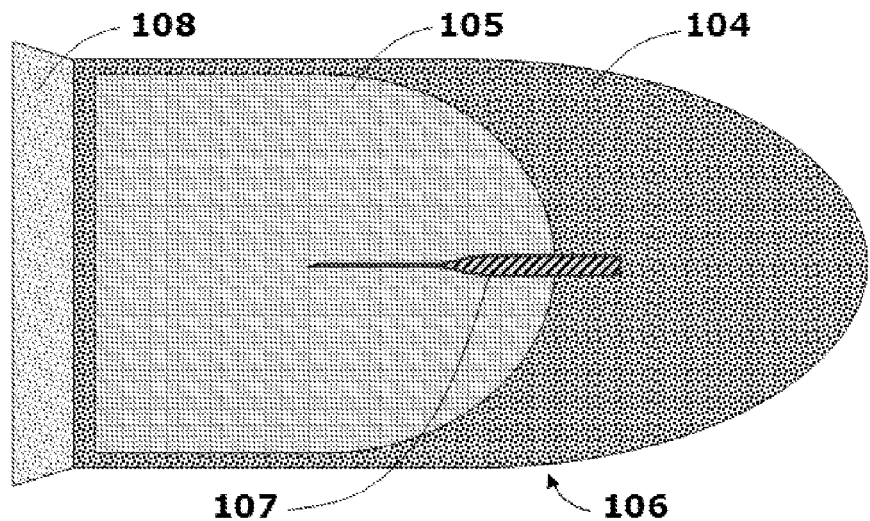

FIGS. 3A through 3C illustrate the invention. In this example, a thin, flexible, single-material substrate 104 shown in FIG. 3A is coated with a strong but releasable adhesive on its underside region in all areas except a tab area 108, shown in FIG. 3C, used for grasping the device. A puncture resistant material 105, shown in FIG. 3B, which can be composed of one or more solid-material layers and/or one or more woven-material layers or other puncture-resistant material, as discussed earlier, is bonded to the upper surface of substrate 104 of FIG. 3A, preferably at least over the position shown in FIG. 3C to reduce expense, although it can be sized to cover the entire upper surface of the substrate 104 to make coverage of the needle-tip area more certain. FIG. 3C shows the complete device 106 which is the object of the invention. An illustration 107 of the end of a typical needle electrode, as shown in FIG. 3C, can be printed on the upper surfaces as a guide to the user so that placement of the needlestick-prevention devices can be optimally positioned over the sharp tips of inserted needle electrodes. Each time a needlestick-prevention device is employed, and its near-optimal position has been established, the user is to apply a gentle force to its entire upper surface to both secure it to the patient's skin and provide a holding force to both the length of electrode lead 103 and the covering 102, as shown in FIG. 1, that its adhesive contacts.

Figure 4:
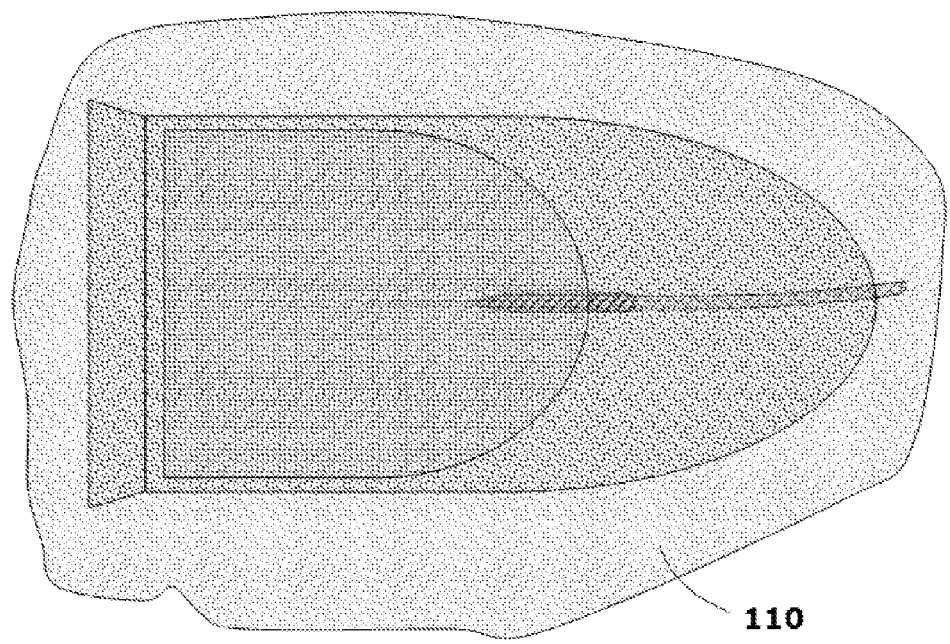

FIG. 4 illustrates a needlestick-prevention device in use, with the needlestick-prevention device shown nearly transparent to indicate the correct position of the device with respect to a needle inserted into the patient's skin 110. Note that the tab, when lifted for removal of the device, will peel away from the patient's skin in such a way that the electrode will tend to be gently pulled-out of the patient's skin in the direction that is least likely to traumatize the layers of skin in which the needle electrode had been placed.

Figure 5:
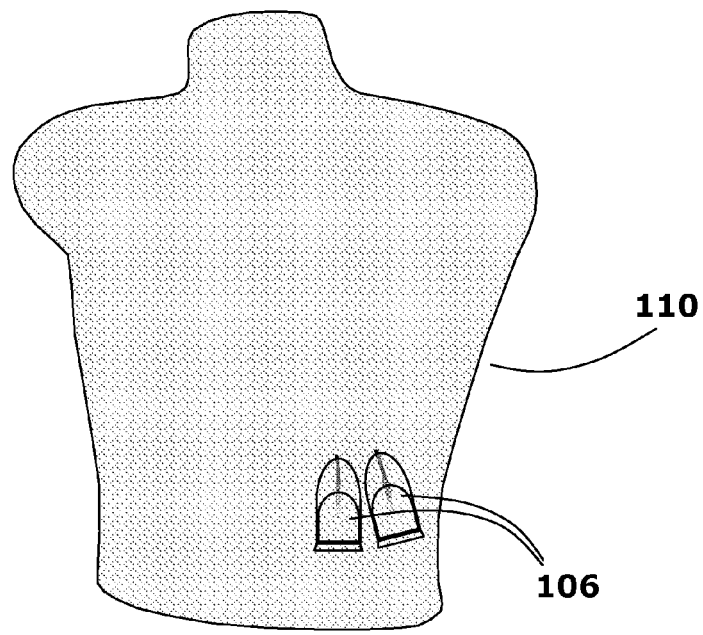

FIG. 5 illustrates the ends of a needle-electrode pair being covered by a pair of needlestick-prevention devices 106 (again shown as nearly transparent to indicate the devices' proper placements over needle electrodes). A large section of the patient's skin 110 is shown to help to exemplify such placements.

Figure 6:
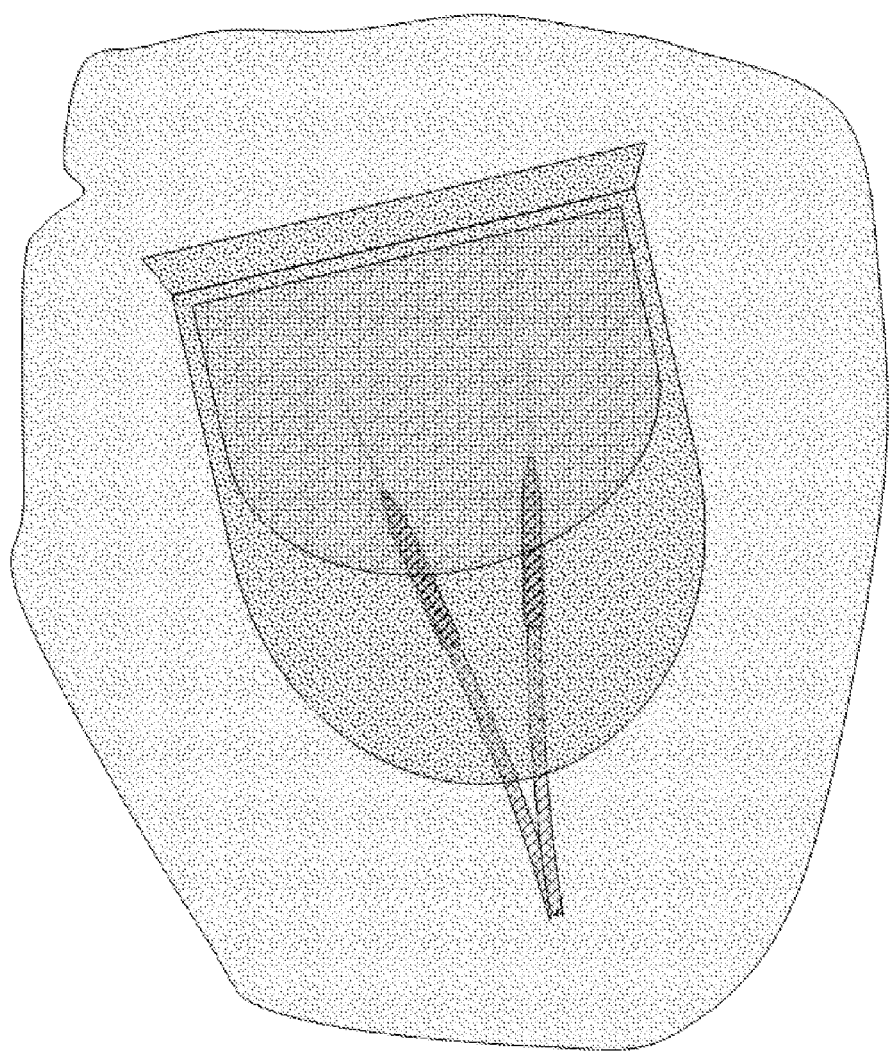

FIG. 6 is an illustration of a wider version of a needlestick-prevention device covering a pair of needle electrodes in an exemplary region in which both needle electrodes are inserted in positions that are closer to each other than they are shown in FIG. 5.

Figure 7:
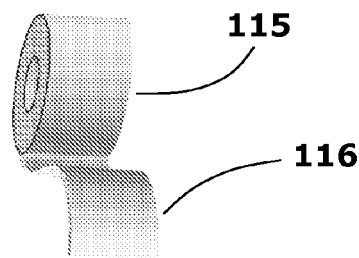

FIG. 7 illustrates a conventional roll of medical-grade adhesive tape 115 like those commonly used in the OR to secure needle electrodes to a patient's body. The tape substrate is generally of single composition so that a length of tape 116 drawn from the roll will contain only the substrate and its adhesive coating deposited on one side only. One can imagine a similarly appearing roll of a long, sufficiently wide release-material-coated ribbon onto which multiple individual needlestick-prevention devices, such as the device herein described, are linearly placed to enable convenient dispensing of the product, and further that the supporting ribbon may be perforated at regions between the individual devices for easy separation from others, singly or in groups, or easily torn for the same purpose. As a possibly obvious modification of the product being supplied on a roll of release-material-coated ribbon, the ribbon could be comprised of, or impregnated with, any of the materials which afford a useful puncture-resistant quality, be coated on one side with any medically useful pressure-sensitive adhesive, and even be printed on the opposite side with any of the markings or warnings described above. In such a configuration the product could be perforated at specific locations along the length of the ribbon or it could be so composed that it could be cut-to-length or torn-to-length, as desired, for each specific application.

Figure 8:
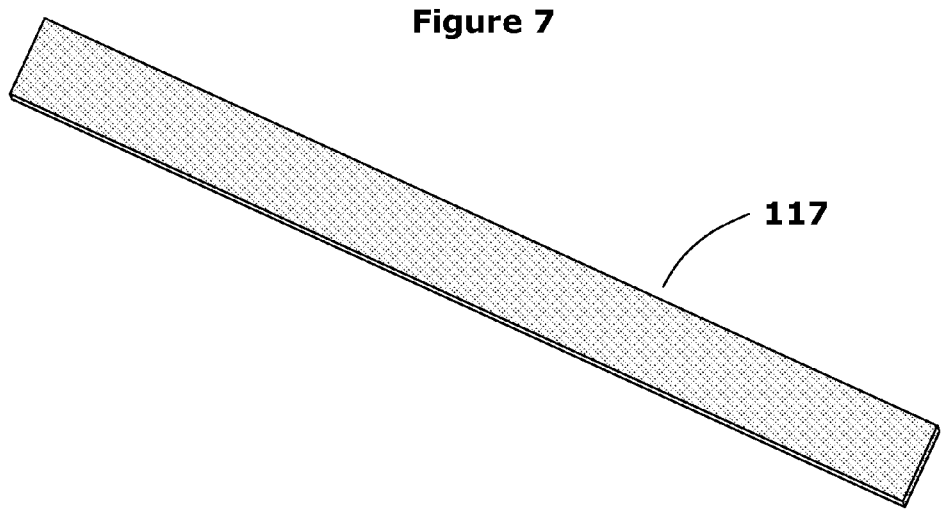

FIG. 8 depicts an example of a length of tape 117 that has been drawn from a tape roll like that shown in FIG. 7.

Figure 9:
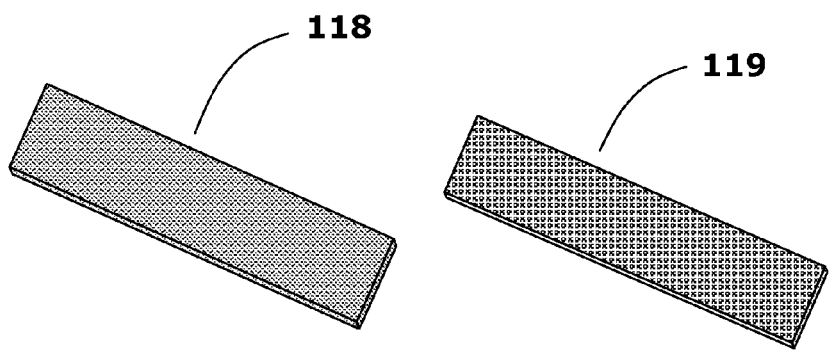

FIG. 9 illustrates two lengths of flexible and different-composition puncture-resistant materials 118 and 119 having approximately equal lengths and having widths approximately equal to the width of the length of tape 117. Lengths of materials like these can be attached to the substrate of a tape roll and have the appearance of the length of tape 120 shown in FIG. 10. These drawings were made to roughly depict a homogeneous material in component 118 and a wire mesh in component 119. As discussed earlier, the tape can be constructed such that the puncture-resistant material is integrated into the substrate.

Figure 10:
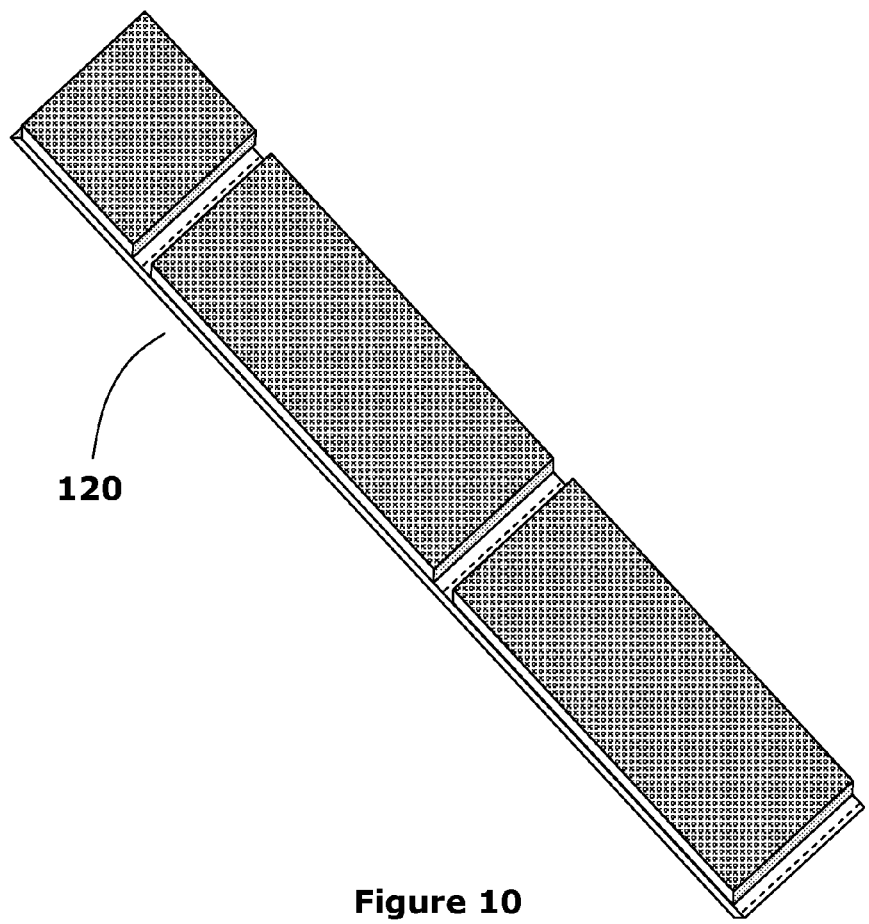

FIG. 10 shows a length of tape 120 composed of a substrate and attached lengths of puncture-resistant material(s). It is also shown with perforations that enable a user to quickly and easily separate consistent lengths of protective coverings from the tape roll.

Figure 11:
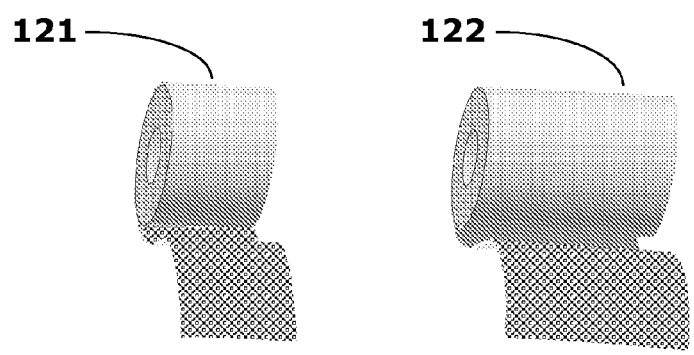

FIG. 11 depicts two different-width tape rolls 121 and 122 that have been processed to have the puncture-resistant material integrated into its substrate.

Figure 12:
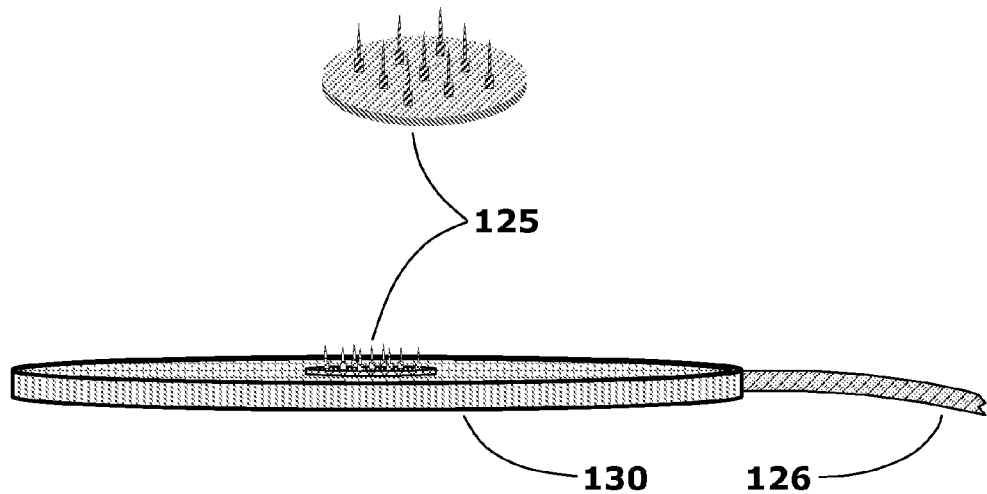

FIG. 12 illustrates the third embodiment of the current invention showing a wired needle-array electrode which has an array of thin, sharp-tipped needles 125 (shown with exaggerated lengths in the upper drawing for clarity) which is electrically connected to an electrode lead 126 and adhesively or otherwise attached to a substrate 130. This substrate is coated, on the side to which the needle array is attached, with a strong, non-permanent pressure-sensitive-adhesive (not shown) that preferably coats the entire region around the needle-array to enable secure attachment to a patient's skin.

Figure 13:
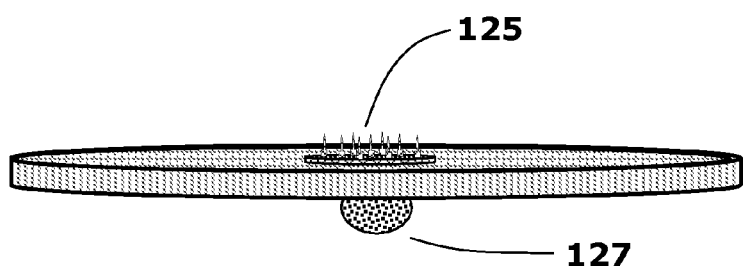

FIG. 13 illustrates a snap-on (or "snap") needle-array electrode that can be identical to the needle-array electrode shown in FIG. 12 except that the array of needles 125 is electrically connected to an electrical connector contact 127 enabling it to be used with reusable snap-electrode leads.

Figure 14:
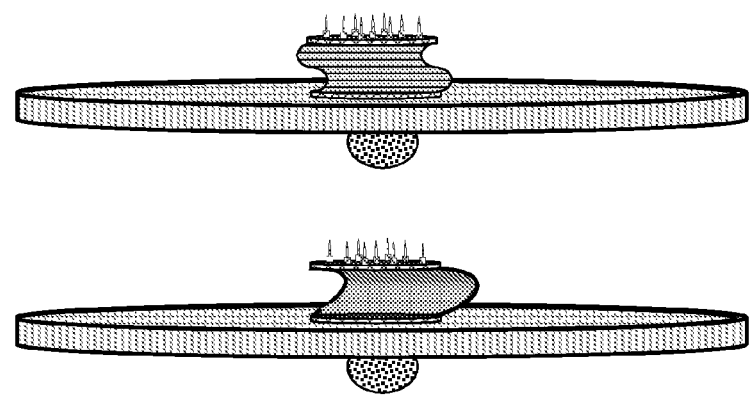

FIG. 14 illustrates the device of FIG. 13 except that with this design, the needle array is mounted to a flexible conductive strap to prevent degradation of the electrical connection to the patient's subdermal tissue that could otherwise occur due to minor movement or lifting of the substrate during use.

BEST MODE FOR CARRYING-OUT THE INVENTION

A variety of materials could be used to resist penetration by a needle electrode. For all of the models of this invention to be practical, all such materials will preferably be flexible and thin enough to meet the needs of their applications and their packaging. Designs of the various models are directed to those that are most cost-effective without compromising function. Other design considerations include safety, efficacy, reliability, ease of use, manufacturability, ergonomic factors, attractiveness, and the ability to maintain position on the patient's skin, the nature of which is itself a variable having a large range in terms of properties that affect the attachment strength of the adhesive bond. Indeed, with the typical 'silk' tape commonly used to secure needle electrodes to a patient's skin, the bonding strength is sometimes so low that one overhears a comment that the patient's skin is like Teflon®; at other times the bonding strength is so strong that one must use care when removing the tape to prevent the patient's skin from being damaged.

The preferable design of the puncture-resistive hat of the first embodiment is a shower-cap-like hair-covering constructed from materials like those mentioned earlier in addition to a finely-woven stainless steel wire mesh reminiscent of a chainmail section of armor but highly flexible and lightweight and capable of being secured around much of a patient's head with embedded elastic material or a drawstring that can be releasably tied. As mentioned earlier, a composition that is suitably conductive and which can be grounded to provide optimal shielding of the electrode leads can be covered with an insulation material so that it can be electrically grounded, if desired, without presenting an electrically grounded area that could be contacted by the patient.

The device of this invention can naturally have any size and shape that achieves the stated function. It can be a near-circular- or near-oval-shaped pad, with or without a convenient tab for grasping it and enabling easy removal, coated on its underside surface with an adhesive similar to that used by snap-electrode manufacturers such as 3M, Vermed, and ConMed. The pad can have a material composition that is puncture-resistant or it can be fabricated with any suitable substrate material within which, or on the outer surface of which is the preferred puncture-resistant material as a coating or structure composed of one layer or multiple layers that can resist penetration by a sharp medical-grade needle or other object for the intended purpose of the invention. The preferred form for a product is as a roll having individual, easily separated sections. The secondary preference for the form based on this embodiment is as a sheet of individual, easily separated, if desirable, sections from which individual devices can be peeled. The device should have an attractive appearance and have colors and patterns that are immediately visible against a patient's skin for easy recognition and reduced likelihood of their being 'missed' when they are to be removed.

The third embodiment of the device eliminates the potential for puncture from single subdermal needles by substituting, for these needle electrodes, an appliance with (preferably) an array of short dermis-penetrating needles which are electrically conductive and electrically connected to an electrode lead or, more preferably, to a snap connector contact for connection to a mating snap connector on a reusable electrode lead. For this embodiment, the array of needles is either directly attached to the substrate as shown in FIG. 13 of this invention's separate Drawing document, or is attached, as shown in the examples depicted in FIG. 14, to one end of a flexible "U"-shaped or "S"-shaped electrically conductive strap, the other end of which is directly attached to the substrate. The substrate and adhesive can be similar to those used by the above-mentioned snap-electrode manufacturers. The devices described in this paragraph must be supplied sterile and easily kept sterile until they are to be applied to a patient's body.

REFERENCES

[1] Estimation of the global burden of disease attributable to contaminated sharps injuries among health-care workers, Priiss-Ustiin A, Rapiti E, Hutin Y. Am J Ind Med. 2005 December; 48(6):482-90. 2005 Wiley-Liss, Inc. PMID: 16299710 [PubMed—indexed for MEDLINE] Protection of the Human Environment, World Health Organization, Geneva, Switzerland. pruessa@who.int.
[2] Wikipedia
[3] Estimation of the global burden of disease attributable to contaminated sharps injuries among health-care workers, Priiss-Ustiin A, Rapiti E, Hutin Y. Am J Ind Med. 2005 December; 48(6):482-90. 2005 Wiley-Liss, Inc. PMID: 16299710 [PubMed—indexed for MEDLINE]
[4] Chalupa S, Markkanen P K, Galligan C J, Quinn M M (March/Aril 2008). "Needlestick and Sharps Injury Prevention: Are We Reaching Our Goals?". *AAACN Viewpoint*
[5] Klein S M, Foltin J, Gomella L G (2003). *Emergency Medicine on Call*. New York: McGraw-Hill. p. 288. ISBN 0071388796
[6] Diprose P, Deakin C D, Smedley J (1 Jun. 2000). "Ignorance of post-exposure prophylaxis guidelines following HIV needlestick injury may increase the risk of seroconversion". *British Journal of Anaesthesia* 2000, 84 (6) 767-770 84 (6): 767. PMID 10895754.
[7] Needlestick injuries during surgical procedures: a multidisciplinary online study, Adams, Simon; Stojkovic, Stevan G.; Leveson, Stephen H. Oxford University Press, Occupational Medicine, Volume 60, Number 2, 2 Mar. 2010, pp. 139-144(6). DOI: 10.1093/occmed/kqp 175.
[8] "Enhancing the Stab Resistance of Flexible Body Armor Using Functionalized $SiO_2$ Nanoparticles" by Floria Eve Clements—16th International Conference on Composite Materials

We claim:

1. A puncture-resistant covering for one or more needle electrodes, each having a sharp end and a lead-wire, the electrodes configured for electrical stimulation or recording of biological electrical potentials in clinical or surgical settings, the covering configured for use while the electrodes are inserted into a body to provide these functions, for the purpose of reducing risk of transferring disease that could result from medical personnel suffering skin-scrape or skin-puncture through contact with the sharp ends of said needles, said covering comprising:
   a puncture-resistant patch of suitable shape and size having a front surface and a rear surface and having a thickness of less than one-quarter inch and having a pressure-sensitive adhesive existing on at least one-half of the rear surface for the purpose of securing the covering to the body and holding-in-place the needle electrode(s) and lead-wire(s) that it covers during its use.

2. The covering of claim 1 wherein at least one region of the covering presents as a tab that is devoid of the adhesive to facilitate its placement and/or removal.

3. The covering of claim 1 wherein, during its use, the front surface contains one or more words and/or designs configured to:
   identify or express caution regarding the existence of the needle electrode(s) which it covers, and/or;
   communicate a preferred orientation of the covering with respect to the covered needle electrode(s) for optimization of its application and/or removal, and/or;
   draw attention to the covering's presence to help ensure that, in the process of removing all the needle electrode (s) with the coverings, the chance of any needle electrode(s) being "missed" would be reduced.

4. The covering of claim 1, further comprising one or more additional layers.

5. The covering of claim 1, further comprising a release liner on the adhesive.

6. A stock of the coverings of claim 1, wherein the stock comprises a plurality of unit coverings provided on sheets or rolls of release material.

7. The stock of claim 6, wherein the release material can be cut, torn, or separated at perforations to yield separate units.

* * * * *